United States Patent [19]

Aoyama et al.

[11] Patent Number: 5,689,019
[45] Date of Patent: Nov. 18, 1997

[54] MANUFACTURING METHOD FOR 1,1,1,2,3,3,3-HEPTAFLUOROPROPANE

[75] Inventors: Hirokazu Aoyama; Noriaki Shibata, both of Settsu, Japan

[73] Assignee: Daikin Industries Ltd., Osaka, Japan

[21] Appl. No.: 765,433

[22] PCT Filed: Jul. 11, 1995

[86] PCT No.: PCT/JP95/01379

§ 371 Date: Jan. 14, 1997

§ 102(e) Date: Jan. 14, 1997

[87] PCT Pub. No.: WO96/02483

PCT Pub. Date: Feb. 1, 1996

[30] Foreign Application Priority Data

Jul. 14, 1994 [JP] Japan ................ 6-185369

[51] Int. Cl.$^6$ ................................................. C07C 17/00
[52] U.S. Cl. .................................................... 570/167
[58] Field of Search ..................................... 570/167

[56] References Cited

U.S. PATENT DOCUMENTS 4,158,023 6/1979 von Halasz .
5,264,639 11/1993 Morikawa ................ 570/167
5,315,046 5/1994 Fernschild .
5,399,795 3/1995 Franz et al. .
5,616,819 4/1997 Boyce ........................ 570/167

FOREIGN PATENT DOCUMENTS 0 634 383 A1 1/1995 European Pat. Off. .
2-17137 1/1990 Japan .

*Primary Examiner*—Alan Siegel
*Attorney, Agent, or Firm*—Armstrong, Westerman, Hattori, McLeland & Naughton

[57] ABSTRACT

A manufacturing method for 1,1,1,2,3,3,3-heptafluoropropane (HFC-227ea) wherein 1,1,1,2,3,3,3-heptafluoropropane (HFC-227ea) is obtained by reacting hexafluoropropene (HFP) with anhydrous hydrogen fluoride (HF) under the presence of antimony catalyst.

A manufacturing method can be provided in which HFC-227ea can be obtained at high yield under the mild condition without producing by-products such as olefin compounds and so on.

9 Claims, No Drawings

MANUFACTURING METHOD FOR 1,1,1,2,3,3,3-HEPTAFLUOROPROPANE

INDUSTRIAL FIELDS WHERE THE INVENTION CAN BE UTILIZED

This invention relates to a manufacturing method for 1,1,1,2,3,3,3-heptafluoropropane which is important for industrial fields as substitutes, for example, as a fire-extinguish-agent (a substitute for halone), a propellant of aerosol, (paticulaly, propellant for medicines) and so on, doesn't destroy ozone in the ozone layer.

PRIOR ART

As a manufacturing method for 1,1,1,2,3,3,3-heptafluoropropane (Hereinafter, this can be called HFC-227ea.), a method by reacting hexafluoropropene with anhydrous HF at 300° to 400° C. under the presence of an active carbon catalyst (U.S. Pat. No. 902590), and a method by reduction of 2-chloro-1,1,1,2,3,3,3-heptafluoropropane at 100° to 400° C. under the presence of a catalyst (E.P. 539989) have been known.

However, under the reaction at higher temperature as such, olefin impurities which are not easy for separation are produced. In this problem a new method for the separation was proposed (E.P. 512502). Paticulaly, since octafluoroisobutene in olefin impurities produced, is a deadly poisonous compound, it needs a lot of cost for charging this compound to harmless substance. And, when the active carbon catalyst is used, olefin impurities are observed that the activity of the catalyst is lowered, and it also needs to reactivate the catalyst (This is disclosed in E.P. 562509).

OBJECTS OF THE INVENTION

The object of this invention is to provide a manufacturing method HFC-227ea wherein it can be obtained at high yield under the mild condition without producing by-products such as olefin compounds etc.

THE CONSTRUCTION OF THE INVENTION

As a result of eagerly studying of the process of a manufacturing method for HFC-227ea, the inventors found a process in which hexafluoropropene (Hereinafter, this can be called HFP.) is reacted with anhydrous HF under the presence of antimony catalyst to obtain 1,1,1,2,3,3,3-heptafluoropropane (HFC-227ea) at high yield even under low temperature. This process has economical advantages that equipments for separation, refinement and harmlessness for olefin impurities are unnecessary because the olefin impurities are not produced at all, thus they have completed this invention.

That is, this invention relates to a manufacturing method for 1,1,1,2,3,3,3-heptafluoropropane (HFC-227ea) wherein 1,1,1,2,3,3,3-heptafluoropropane (HFC-227ea) is obtained by reacting HFP with anhydrous HF under the presence of antimony catalyst.

In the manufaturing process of this invention, particularly, it is important that the reaction is conducted by using antimony catalyst in liquid phase to obtain HFC-227ea at high yield and under the mild condition, and this process has a novelty that thoroughly differs from the prior arts.

As the above antimony catalyst, pentavalent antimony, trivalent antimony or the mixture of these can be used.

In this case, fluorinated-chlorinated antimony which is obtained by fluorination of antimony pentachloride or antimony trichloride can be used as a catalyst. However, when some chlorine atoms are contained in the catalyst, chlorination of HFP may be conducted to lower the selectivity of this reaction. Accordingly, it is preferable to use completely fluorinated antimony such as antimony pentafluoride and antimony trifluoride as the catalyst. Antimony pentafluoride or antimony trifluoride can be used either alone or mixed each other.

In the manufacturing process of this invention, solvent is not specifically necessary, but anhydrous HF being a reaction material can be used as the solvent. Reaction solvent is needed, to be inactive to the catalyst. For example, perfluoro-compounds such as perfluorohexane, perfluorodecaline, perfluorotributylamine and so on are given.

Using antimony pentafluoride as the catalyst and anhydrous HF as the reaction solvent may restrict the concentration of the antimony catalyst according to the materials of the reaction container due to the storong corrosiveness. When the reaction container is made of fluorocarbon resins, the concentration of the catalyst is not restricted in use. However, when the reaction container made of anticorrosion substance such as Hastelloy C22 and so on limits the concentration of the catalyst is limited. In the case of using antimony pentafluoride alone as the catalyst, the concentration is preferably not more than 1 mol % to the amount of anhydrous HF, and more preferably not more than 0.5 mol % in view of the corrosion.

When the mixture of antimony pentafluoride and antimony trifluoride is applied, the mixing ratio of antimony pentafluoride to antimony trifluoride is preferably not more than 1 at molar ratio, more preferably not more than 0.5, and the concentration of the mixture of antimony fluoride is preferably not more than 10 mol % to the amount of anhydrous HF, more preferably not more than 3 mol % in view of the corrosion.

Using antimony trifluoride alone as the catalyst and anhydrous HF as the reacting solvent would not limit the concentration of the catalyst because the corrosiveness is very small.

Besides, in this invention, in order to avoid the problem of corrosion, the reaction condition can be adopted in which an amount of anhydrous HF is not charged in the reaction system by adding HFP and anhydrous HF to antimony pentafluoride continuously, and taking out the produced HFC-227ea and unreacted anhydrous HF and/or HFP from the reaction system continuously.

Reaction temperature may not specifically be limited, but it is preferably not more than 100° C. in view of suppressing the production of octafluoroisobutene and so on, more preferably 25° to 100° C., and further more preferably 40° to 80° C.

Also, reaction pressure may not specifically be restricted, but it's range is preferable from atmospheric pressure to 50 kg/cm$^2$G. More preferably the range from atmospheric pressure to 30 kg/cm$^2$G can be adopted.

The molar ratio of HFP and anhydrous HF can be optionally varied. When an amount of anhydrous HF is not more than the stoichiometric amount needed for the reaction, unreacted HFP is discharged from the reaction system with HFC-227ea, however, this HFP can be recovered with HFC-227ea after separation and recycled to the reaction system. And, when an amount of HFP is not more than the stoichiometoric amount needed for the reaction, unreacted HF may be discharged from the reaction system with HFC-227ea, however, this HF can also be recycled to the reaction system after separation.

As reaction systems, there can be applied a batch system wherein the reaction is conducted after supplying the raw materials so as to recover the products and so on, a semi-batch system wherein a kind of the raw material is supplied continuously and the products and so on are taken out continuously, and a continuous system wherein the raw materials are supplied continuously and the products and so on are taken out continuously.

THE POSSIBILITY OF UTILIZING THE INVENTION IN INDUSTRY

In this invention, by reacting HFP with anhydrous HF under the presence of antimony catalyst, 1,1,1,2,3,3,3-heptafluoropropane (HFC-227ea) can be obtained at high yield with no olefin compounds which is difficult to be removed. Therefore a manufacturing method for HFC-227ea having economical advantages can be provided. This 1,1,1,2,3,3,3-heptafluoropropane (HFC-227ea) can not only be a fire-extinguish agent, refrigerants, a blowing agent without destroying ozone in ozone layer, but also can be utilized as a propellant of aerosol, paticularly for medicines.

EMBODIMENTS

The invention will be explained more concretely in the following examples.

EXAMPLE 1

2.0 g of $SbF_5$ was charged into a 200 mL Hastelloy C22 made autoclave. Then, after cooled at −30° C., 50 g of anhydrous HF and 20 g of HFP were added, and thereafter returned to room temperature, the reaction was continued for 20 hours with stirring.

Then unreacted HFP and reaction products were led to water-washing tower and alkaline-washing tower from the above stated autoclave, in which acid components were removed, the remains were captured with a trap cooled at −70° C. Captured organic compounds were analyzed with a gas chromatography under the following conditions.
<Analysis conditions>
  Column: liquid phase 5% FLUORCOL
  carrier CARBOPACK B 60/80mesh
  filled column length 3 m of stainless-made
Analysis condition on raising temperature:
  holding for 25 minutes at 50° C.,
  raising speed of 5° C./min for 200° C.
Detector: FID As a result of analysis, the conversion of HFP was 35%, the selectivity to HFC-227ea was not less than 99.9%, and olefin compounds having four or more carbon atoms were not observed.

EXAMPLE 2

After 4.0 g of $SbF_5$, 95 g of anhydrous HF and 40 g of HFP were charged in the same reaction tube as Example 1, the reaction was carried for 8 hours at 50° C. And, as a result of same analyzing as Example 1, the conversion of HFP was 99%, the selectivity to HFC-227ea was not less than 99.9%, and olefin compounds having four or more carbon atoms were not observed.

EXAMPLE 3

5.4 g of $SbF_5$ and 8.9 g of $SbF_3$ were charged instead of $SbF_5$ in Example 1, to carry out the reaction as described in Example 1. As a result of same analyzing as Example 1, the conversion of HFP was 44%, the selectivity to HFC-227ea was almost 99.9% or more, and olefin compounds having four or more carbon atoms were not observed.

EXAMPLE 4

15.0 g of $SbF_5$ was charged into a 200 mL SUS 316 autoclave with an inner tube made of polytetrafluoroethylene (PTFE). Then, after cooled at −30° C., 40 g of anhydrous HF and 50 g of HFP were added, returned to room temperature, the reaction was continued for 4 hours at 50° C. with stirring.

After cooled to room temperature, unreacted HFP and reacted products were led to water-washing tower and alkaline-washing tower from the above stated autoclave, in which the products were captured with a trap cooled at −70° C., as removing HF. Captured organic compounds were analyzed with a gas chromatography, as mentioned in Example 1.

As a result of analysis, the conversion of HFP was 99.8%, the selectivity to HFC-227ea was not less than 99.9%, and olefin compounds having four or more carbon atoms were not observed.

Then, after 40 g of anhydrous HF and 50 g of HFP were added again in the reaction tube where the catalyst was remained, the reaction was carried as same as above stated, the conversion of HFP was 99.8%, the selectivity to HFC-227ea was not less than 99.9%, and olefin compounds having four or more carbon atoms were not observed.

Comparative example 1

8.8 g of coconut shell active carbon (Yashicoal-M, made by Taihei Kagaku Sangyo Co., Ltd.) was added in a reactor tube made of Hastelloy-C (20 mm of inner diameter), then the reactor was heated at 400° C. for 5 hours while nitrogen gas was flowed. As holding the temperature at 400° C., HF in gaseous state was passed at flowing rate of 125 mL/min for 2 hours, then HFP was added into HF flow, at flowing rate of 50 mL/min.

After the gas from the reactor tube outlet was led to water-washing tower and alkaline-washing tower to remove HF, it was dried with calcium chloride. At 3 hours were passed after hexafluoropropene was started to flow, the gas from the reactor tube outlet was washed and analyzed with a gas chromatography as mentioned in Example 1.

As a result of analysis, the conversion of hexafluoropropene was 99.8%, the selectivity to HFC-227ea was 99.3%, and 0.68% for compounds having four or more carbon atoms (containing olefin compounds). The compounds also contained 258 ppm of octafluoroisobutene.

What is claimed is:

1. A manufacturing method for 1,1,1,2,3,3,3-heptafluoropropane wherein 1,1,1,2,3,3,3-heptafluoropropane is obtained by reacting hexafluoropropene with anhydrous hydrogen fluoride under the presence of antimony catalyst.

2. A manufacturing method as defined by claim 1 wherein the antimony catalyst consists of pentavalent antimony, trivalent antimony or the mixture.

3. A manufacturing method as defined by claim 1 or 2 wherein the antimony catalyst consists of antimony pentafluoride, antimony trifluoride or the mixture.

4. A manufacturing method as defined by claim 3 wherein the mixing ratio of antimony pentafluoride and antimony trifluoride is antimony pentafluoride/antimony trifluoride $\leq 1$ at molar ratio.

5. A manufacturing method as defined by claim 1 or 2 wherein the antimony catalyst consists of antimony pentafluoride.

6. A manufacturing method as defined by any one of claim 1 or 2 wherein the reaction is conducted in liquid phase.

7. A manufacturing method as defined by claim 1 or 2 wherein the reaction is conducted by using anhydrous hydrogen fluoride as solvent.

8. A manufacturing method as defined by claim 1 or 2 wherein hexafluoropropene and anhydrous hydrogen fluoride are added and reacted continuously to antimony pentafluoride, and produced 1,1,1,2,3,3,3-heptafluoropropane and unreacted hexafluoropropene and/or unreacted hydrogen fluoride are taken out from reaction system continuously.

9. A manufacturing method as defined by claim 1 or 2 wherein the reaction is carried out at the temperature of not more than 100° C.

* * * * *